United States Patent [19]

Barron

[11] Patent Number: 4,950,226

[45] Date of Patent: Aug. 21, 1990

[54] SURGICAL SHUNT FOR LIVER ISOLATION

[76] Inventor: Bruce Barron, P.O. Box 430, Spruce Pine, N.C. 28777

[21] Appl. No.: 405,765

[22] Filed: Sep. 11, 1989

[51] Int. Cl.$^5$ ............................................. A61M 1/00
[52] U.S. Cl. ....................................... 604/8; 604/101; 604/158
[58] Field of Search ...................... 604/8–10, 604/158, 161, 162, 164, 165, 101, 282; 600/31; 606/192, 194

[56] References Cited

U.S. PATENT DOCUMENTS

| | | | |
|---|---|---|---|
| 3,331,371 | 7/1967 | Rocchi et al. | 604/96 |
| 3,516,408 | 9/1967 | Montanti | 604/8 X |
| 3,889,685 | 6/1975 | Miller, Jr. et al. | 604/8 |
| 4,100,246 | 7/1978 | Frisch | 604/101 X |
| 4,192,302 | 3/1980 | Boddie | 604/8 |
| 4,230,108 | 10/1980 | Young | 604/101 X |
| 4,696,668 | 9/1987 | Wilcox | 604/101 X |

OTHER PUBLICATIONS

Theodore Schrock, M.D.; F. William Blaisdell, M.D. and Carleton Mathewson, Jr., M.D., "Management of Blunt Trauma to the Liver and Hepatic Veins," *Arch. Surg.*, vol. 96, pp. 698–703 (May 1968).
Robert E. Allen, Jr., M.D. and F. William Blaisdell, M.D., "Injuries to the Inferior Vena Cava," *Surgical Clinics of North America*, vol. 52, No. 3, pp. 699–711 (Jun. 1972).
Donald D. Trunkey, M.D., G. Tom Shires, M.D., Robert McClelland, "Management of Liver Trauma in 811 Consecutive Patients,"*Ann. Surg.* vol. 179, No. 5, pp. 722–728 (May 1974).
W. Wilson Defore, Jr. M.D.; Kenneth L. Mattox, M.D.; George L. Jordan, Jr. M.D.; Arthur C. Beall, Jr., M.D., "Management of 1,590 Consecutive Cases of Liver Trauma," *Arch. Surg.*, vol. 111, pp. 493–497 (Apr. 1976).
David B. Pilcher, M.D., P. Kent Harman, B.A., Ernest E. Moore, Jr. M.D., "Retrohepatic Vena Cava Balloon Shunt Introduced Via The Sapheno–Femoral Junction," *The Journal of Trauma*, vol. 17, No. 11, pp. 837–841 (Nov. 1977).
Ernest E. Moore, M.D., Ben Eiseman, M.D., Ernest L. Dunn, M.D., "Current Management of Hepatic Trauma," *Contemporary Surgery*, vol. 15, pp. 91–115 (Sep. 1979).

*Primary Examiner*—Robert A. Hafer
*Assistant Examiner*—Lynda M. Cofsky
*Attorney, Agent, or Firm*—Shefte, Pinckney & Sawyer

[57] ABSTRACT

A shunt for isolating the liver and hepatic veins from normal blood reperfusion into the inferior vena cava during trauma and similar surgical operations includes an outer tube with a first inflatable balloon at one end and a second inflatable balloon at an intermediate location with multiple openings spaced along the tube between the second cuff and the opposite end, and an inner tube telescopically movable within the outer tube with plural sealing O-rings spaced therealong in correspondence to the openings in the outer tube. During surgery, the balloon end of the tube is inserted and advanced upwardly in the inferior vena cava through a venotomy formed at a selected location, either above or below the renal veins. The first balloon is positioned within the right atrium of the heart, inflated, and then drawn backwardly to seat in sealing engagement at the atrial-caval opening. Alternatively, the first balloon may be positioned and inflated within the supradiaphragmatic cava. The second balloon is sufficiently spaced to be disposed below the hepatic veins so that, when also inflated, the liver and hepatic veins are isolated from blood reperfusion into the inferior vena cava. Withdrawal of the inner tube opens one or more of the openings in the outer tube to allow normal reperfusion from the renal veins and the lower extremities into the interior of the outer tube for flow into the right atrium of the heart.

10 Claims, 4 Drawing Sheets

SURGICAL SHUNT FOR LIVER ISOLATION

BACKGROUND OF THE INVENTION

The present invention relates generally to surgical devices and, more particularly, to shunts utilized in human surgical procedures for diverting normal blood flow.

The frequency of relatively complicated, traumatic vascular injuries has increased significantly in recent history, due in large part to increases in crime rates, high speed automobile accidents, and the like. Injuries to the liver, its hepatic veins, and the inferior vena cava, which leads therefrom to the right atrium of the heart, present significant technical problems to the surgeon in controlling blood loss preparatory to actual repair of the specific injuries. Indeed, major hospitals across the United States consistently report substantially high mortality rates in surgically treating traumatic vascular injuries of this type to the abdominal area. Furthermore, most deaths resulting from such injuries are caused by exsanguination, i.e. excessive blood loss.

Obviously, in emergency surgical procedures to treat hepatic and caval injuries of this type, time is of the essence to the surgeon in initially controlling blood loss. Disadvantageously, however, conventional surgical techniques for doing so are relatively time consuming and, moreover, require substantial experience and skill often possessed only by trauma surgery specialists. Basically, these techniques seek to shunt blood flow around the injured regions of the inferior vena cava and, in the case of liver, retro hepatic caval and hepatic vein injuries, around the injured hepatic caval area to isolate the liver and hepatic veins from reperfusive blood flow into the vena cava.

One conventional technique for accomplishing these purposes is to form an incision in the right atrial appendage of the heart and insert a tubular catheter downwardly through the right atrium and the inferior vena cava. The catheter is of a sufficient length that its distal end extends to approximately the location at which the renal veins from the kidneys open into the vena cava. A side opening is formed in the portion of the catheter which is disposed within the right atrium of the heart. The proximal end of the shunt extends outwardly from the right atrial appendage and is either clamped or utilized for fluid infusions. To isolate the liver and hepatic veins, tourniquets of umbilical tapes must be placed about the vena cava at locations above and below the hepatic veins. This procedure was first proposed by Drs. Schrock, Blaisdell, and Mathewson in a published article entitled, "Management of Blunt Trauma to the Liver and Hepatic Veins", *Arch. Surg.*, Volume 96, pages 698-704 (May 1968).

An alternative procedure utilizes a tubular shunt having an inflatable balloon at one end. The balloon end of the shunt is inserted in the groin area of the patient at the saphenofemoral junction and therefrom advanced upwardly through the inferior vena cava until the balloon is located at the hepatic vein junction, whereupon the balloon is inflated to isolate the hepatic veins and liver. Side openings in the shunt permit otherwise normal blood reperfusion through the inferior vena cava to flow through the shunt. The proximal end of the shunt extends outwardly from the saphenofemoral junction and may be utilized for intravenous infusions. This procedure was suggested by Drs. Pilcher, Harman, and Moore, in *The Journal of Trauma*, "Retrohepatic Vena Cava Balloon Shunt Introduced Via The Sapheno-Femoral Junction", Volume 17, Number 11, pages 837-841 (November 1977).

A similar technique is discussed by Drs. Trunkey, Shires and McClelland, in "Management of Liver Trauma in 811 Consecutive Patients", *Ann. Surg.*, Volume 179, Number 5, pages 722-728 (May 1974). A tubular catheter having an inflatable balloon at one end is also utilized in this technique. Initially, tourniquets of umbilical tape are placed around the suprarenal area of the inferior vena cava and a venotomy formed in the cava between the tourniquets. The shunt is cut to a length estimated to correspond to the caval length between the diaphragm and a point below the venotomy for the particular patient. After releasing the superior tourniquet, the balloon end of the shunt is inserted through the venotomy and advanced upwardly through the vena cava to the patient's diaphragm, whereupon the balloon is inflated to occlude the hepatic caval openings. The opposite, proximal end of the shunt is inserted through the venotomy immediately after release of the inferior tourniquet. Each tourniquet is then reapplied to control bleeding.

While these techniques have significantly advanced the practice of trauma surgery and improved the mortality experience thereof, concern still exists that these procedures require a level of experience and skill generally not possessed by non-trauma surgeons and, furthermore, may be overly time-consuming. Accordingly, a need exists for a suitable means of shunting the inferior vena cava during trauma surgery to isolate the hepatic veins and liver which may be easily and quickly employed by substantially any surgeon.

SUMMARY OF THE INVENTION

Briefly summarized, the present invention provides a shunt usable in human surgical operations for isolating the liver and its hepatic veins from normal reperfusion of blood through the inferior vena cava to the heart and also from backflowing of blood downstream through the inferior vena cava. Basically, the shunt comprises an outer tube having a leading end for insertion into and advancement through the inferior vena cava at a selected retrohepatic (i.e., downstream of the hepatic veins) venotomy location, either above or below the renal veins, to a location upstream of the hepatic veins and having a trailing end for disposition outside the inferior vena cava. A first radially outwardly expansible cuff is affixed to the outer tube adjacent its leading end for sealing engagement with the inferior vena cava at the upstream location above the diaphragm. A second radially outwardly expansible cuff is similarly affixed to the outer tube at an intermediate location therealong spaced from the first cuff for sealing engagement with the inferior vena cava at a location downstream of the hepatic veins and upstream of the venotomy location. The outer tube has at least one opening formed therethrough between the second cuff and the trailing end for disposition within the lumen of the inferior vena cava. An inner tube is telescopically movable within the outer tube and has an operating end extending outwardly from the trailing end of the outer tube for actuating movement of the inner tube relative to the outer tube. At least a pair of annular sealing rings are respectively attached exteriorly to the inner tube at a spacing therealong greater than the lengthwise extent of the opening in the outer tube. Accordingly, when the shunt is inserted as described into the inferior vena cava, the expansible cuffs prevent blood reperfusion through the inferior vena cava between the hepatic veins and the heart as well as preventing backflow of blood downstream through the inferior vena cava, while selective movement of the inner tube with respect to the outer tube allows opening and closing of the opening in the outer tube to selectively control fluid communication between the inferior vena cava and the interior of the outer tube for controlling normal blood reperfusion from the lower extremities of the patient.

With many patients, it is contemplated to be desirable that the shunt be advanced through the inferior vena cava to dispose the leading end of the outer tube and the first cuff within the right atrium of the heart so that the first cuff can be seated in sealing engagement at the atrial-caval opening at the juncture between the inferior vena cava and the right atrium of the heart. However, in many patients, the length of the inferior vena cava between the hepatic veins and the heart will be sufficient to enable the first cuff to be positioned within the lumen of the inferior vena cava at a location above the diaphragm intermediate the hepatic veins and the heart without requiring that the cuff be advanced fully into the right atrium of the heart.

In the preferred embodiment of the shunt, the spacing of the second cuff from the first cuff is selected so that the second cuff is disposed downstream of the hepatic veins and upstream of the renal veins from the kidneys when the first cuff is seated within the right atrium of the heart in sealing engagement with the atrial-caval opening or in the supradiaphragmatic area of the cava. The outer tube preferably has a plurality of openings formed therethrough at spacings along its length, at least one of the openings being sufficiently adjacent to the second cuff to be at or upstream of the renal veins for blood reperfusion from the kidneys and their renal veins into the interior of the outer tube when the inner tube is moved to open the one opening in the outer tube. A plurality of the sealing rings are attached at spacings exteriorly to the inner tube in correspondence to the spacing of the plural openings in the outer tube.

Each cuff is preferably inflatable to facilitate its radial expansibility. Suitable means are associated with the outer tube for defining respective passageways communicating with the first and second cuffs for admitting thereinto and exhausting therefrom inflating fluid. Preferably, the passageways are formed in the annular wall of the outer tube and open therefrom into the respective cuffs.

The operating end of the inner tube is closed by an impermeable but penetrable membrane to prevent blood loss through the inner tube while permitting selective fluid injections into the inner tube. Preferably, the inner and outer tubes are formed of a plastic or other suitably flexible material to facilitate insertion into and advancement through the vena cava.

DESCRIPTION OF THE PREFERRED EMBODIMENT

Figure 1:
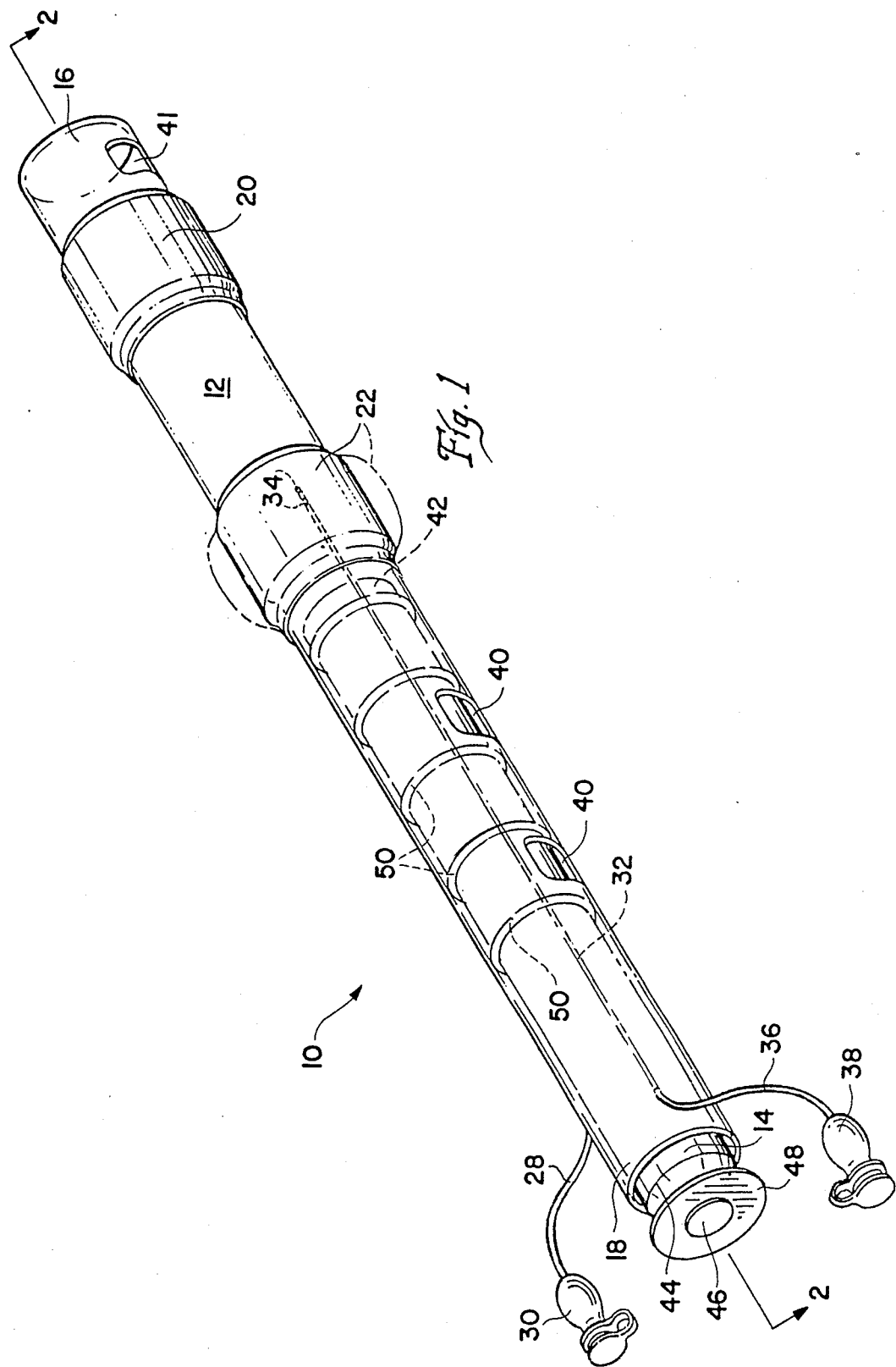
FIG. 1 is a perspective view of a surgical shunt according to the preferred embodiment of the present invention.
Figure 2:
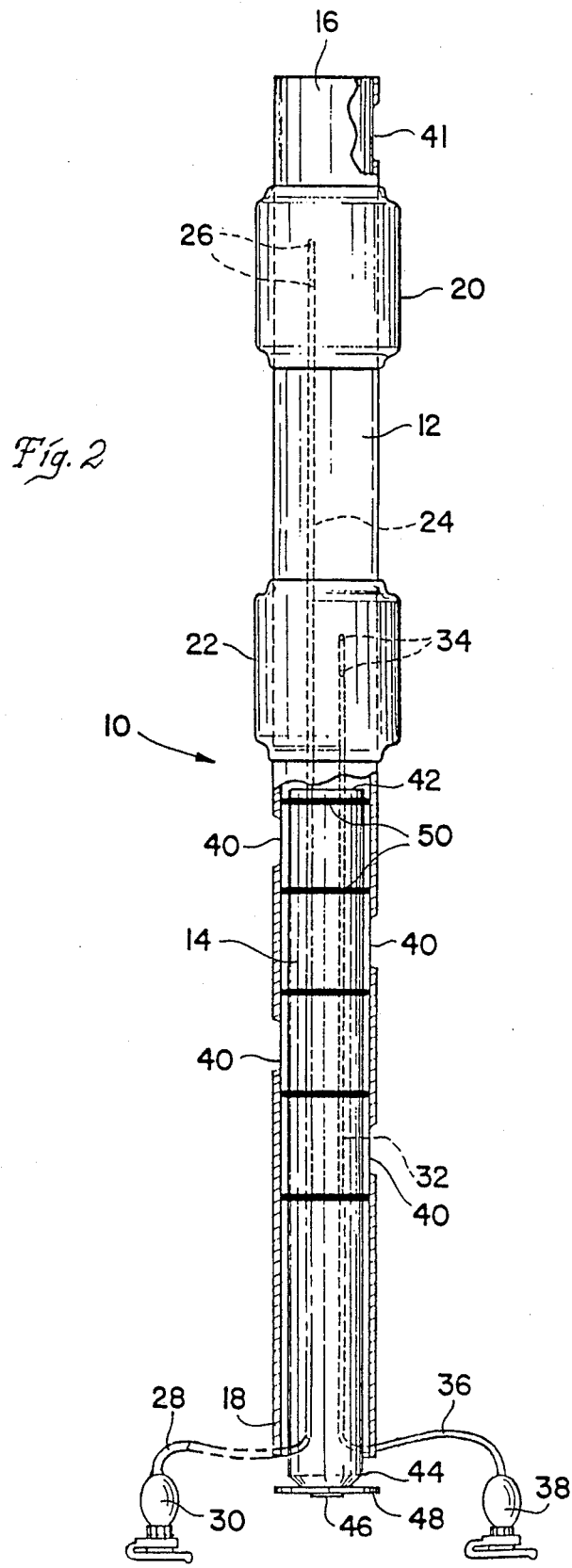
FIG. 2 is a view partially in side elevation and partially in longitudinal cross-section of the shunt of FIG. 1, taken along line 2—2 thereof.

Referring now to the accompanying drawings and initially to FIGS. 1 and 2, the surgical shunt according to the preferred embodiment of the present invention is indicated generally at 10 and basically includes an outer tube 12 and an inner tube 14 telescopically received within the outer tube 12 for sliding movement axially with respect thereto. The inner and outer tubes are preferably fabricated of a relatively flexible plastic material, such as a polyvinyl plastic tubing or any other plastic, synthetic or other suitable material utilized in other surgical implements and the like.

The outer tube 12 is open at its opposite leading (distal) and trailing (proximal) ends 16, 18 respectively. A radially outwardly expansible cuff 20, preferably in the form of an inflatable balloon, is affixed exteriorly to the outer tube 12 closely adjacent its leading end 16. Similarly, another radially outwardly expansible cuff 22, also preferably in the form of an inflatable balloon, is affixed exteriorly to the outer tube 12 at an intermediate location therealong spaced from the first cuff 20.

A passageway 24 is formed lengthwise through the annular wall of the outer tube 12 from a location closely adjacent its trailing end 18 to a location adjacent the cuff 20 at the leading end 16 of the tube 12, whereat the passageway 24 communicates with the interior of the cuff 20 through one or more opening 26 formed laterally outwardly through the annular wall of the outer tube 12 at the cuff 20. The opposite end of the passageway 24 adjacent the trailing end 18 of the tube 12 communicates with an auxiliary tube 28 extending radially outwardly from the outer tube 12. A bulb portion 30 is provided at the outer free end of the auxiliary tube 28 to facilitate admission and exhaustion of inflating air for delivery to and from the balloon 20 and to prohibit deflation of the balloon 20 while the shunt 10 is in use.

In like manner, a passageway 32 is formed lengthwise through the annular wall of the outer tube 12 from generally the same location adjacent the trailing end 18 of the outer tube 12 to a location adjacent the cuff 22, whereat the passageway 32 communicates with the interior of the cuff 22 through one or more openings 34 extending laterally outwardly through the annular wall of the outer tube 12. An auxiliary tube 36 communicates with the passageway 32 at the trailing end 18 of the outer tube 12 and extends radially outwardly from the outer tube 12 with a bulb portion 38 at the free end of the auxiliary tube 36 for admitting and exhausting inflating air for delivery to and from the cuff 22 and t prohibit deflation of the cuff 22 while the shunt 10 is in use.

A plurality of openings 40 are formed through the annular wall of the outer tube 12 at substantially equal spacings u along its length between the trailing end 18 and the cuff 22. Preferably, the openings 40 are alternately formed at diametrically opposite sides of the tube 12. Another opening 41 is formed in the annular wall of the outer tube 12 intermediate its leading end 16 and the first cuff 20.

The inner tube 14 is of a substantially shorter length than the outer tube 12 corresponding approximately to the length of the outer tube 12 from its trailing end 18 to the cuff 22. The leading (distal) end 42 of the inner tube 14 is open, while the trailing (proximal) end 44 of the tube 14 is closed by a membrane 46, with an annular collar portion 48 extending radially outwardly from the trailing end 44 to act as a stop to prevent full insertion of the inner tube 14 into the outer tube 12. A plurality of annular sealing O-rings 50 are affixed to the outer periphery of the inner tube 14 along the lengthwise extent thereof corresponding to the lengthwise extent of the outer tube 12 wherein the openings 40 are formed, with the O-rings 50 being arranged at suitable longitudinal spacings at least slightly greater than the longitudinal dimensions of the openings 40 to correspond therewith so that a pair of the O-rings 50 is disposed at each opposite leading and trailing side of the openings 40 with the inner tube 14 inserted into the outer tube 12 to the maximum extent, as best seen in FIG. 2 The O-rings 50 are of a sufficient radial dimension to extend from the outer periphery of the inner tube 14 into sealing contact with the interior periphery of the outer tube 12, the O-rings 50 being formed of a material which is relatively resilient and of a sufficiently low coefficient of friction to facilitate easy sliding contact with the interior surface of the outer tube 12.

Figure 3:
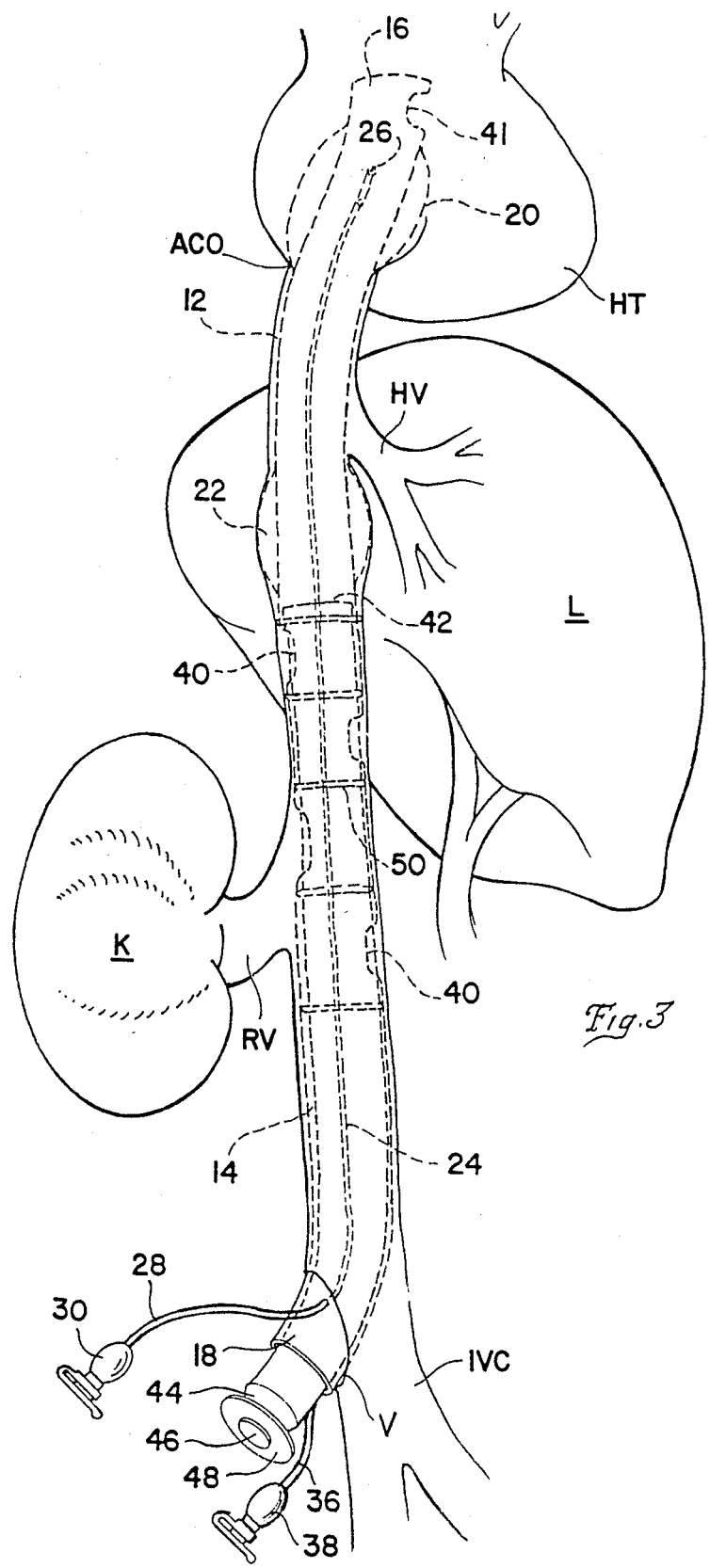
FIG. 3 is a diagrammatic view of the shunt of FIGS. 1 and 2 as inserted in the inferior vena cava of a patient during a representative surgical operation.
Figure 4:
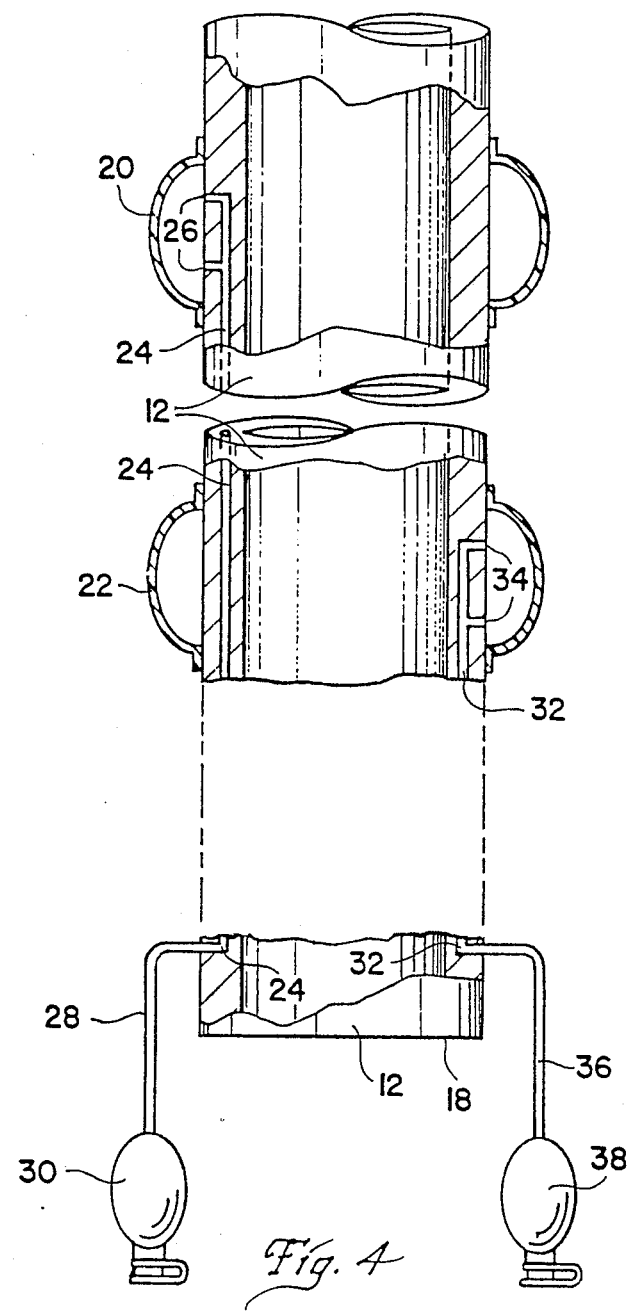
FIG. 4 is an enlarged fragmentary longitudinal cross-sectional view of the outer tube similar to FIG. 2 showing the inflating passageways to the cuffs.

The use and operation of the shunt 10 may thus be understood with reference to FIG. 3 wherein the shunt 10 is illustrated as inserted into the inferior vena cava IVC of a patient during one representative surgical operation requiring isolation of the liver L and hepatic veins HV. As is well known, the inferior vena cava IVC is the major vein of the human body by which blood flow from the iliac veins, the lower extremities and the abdominal area is returned to the heart HT, the terminal distal end of the inferior vena cava IVC opening into the right atrium of the heart Each of the kidneys K of the human body return blood flow through respective renal veins RV which open into the inferior vena cava IVC downstream of the hepatic veins HV from the liver L. For sake of simplicity, only one of the kidneys K and its renal vein RV is shown in the diagram of FIG. 3.

As aforementioned, the shunt 10 of the present invention is utilized during surgical operations to isolate the liver L and its hepatic veins HV temporarily from blood reperfusion into and through the inferior vena cava IVC when traumatic vascular injury to the liver and/or the hepatic veins and/or the adjacent extent of the vena cava causes hemorrhaging. As will of course be understood, the surgical procedure is initiated by opening the patient's abdomen and packing the retro-hepatic area, opening widely the gastro-hepatic momentum, and cross-clamping the aorta (not shown in the drawings) beneath the diaphragm. A conventional Pringle maneuver is performed and the duodenum is widely mobilized. The inferior vena cava IVC then being well exposed in the surgical field, the vena cava is clamped, occluded or otherwise compressed at a location downstream of the hepatic veins HV, which may be upstream or downstream of the renal veins RV, depending upon the injuries, to temporarily stop blood reperfusion in the cava. A Kocher maneuver is performed, after which a purse string suture or a suture with pledgets is made in the inferior vena cava IVC above the clamping location.

A venotomy is then formed in the inferior vena cava IVC at the suture location and, while continuing to occlude or compress the inferior vena cava IVC, the shunt 10 is inserted by the leading end 16 of the outer tube 12 through the venotomy V and advanced superiorly through the inferior vena cava IVC into the right atrium of the heart. Thereupon, the balloon of the first cuff 20 is inflated by admitting air or another inflating fluid through the bulb 30, e.g., utilizing a syringe, and the shunt 10 is withdrawn slightly to seat the cuff 20 in sealing contact with the atrial-caval opening ACO. Next, the balloon of the cuff 22 is likewise inflated into sealing contact with the interior wall of the inferior vena cava IVC downstream of the hepatic veins HV. Accordingly, the cuffs 20, 22 thereby isolate the hepatic area of the inferior vena cava to prevent blood flow both forwardly and backwardly through the inferior vena cava IVC from the hepatic veins HV and the liver L. Tension is continuously maintained on the sutures at the venotomy location to prevent blood loss through the venotomy and to help secure the tube in place.

At this point, the aorta is slowly unclamped. The inner tube 14 may then be withdrawn to open one or more or all of the openings 40 along the extent of the outer tube 12 lying within the lumen of the inferior vena cava IVC, thereby opening the interior of the outer tube 12 to fluid communication with the inferior vena cava IVC below the cuff 22. The inferior vena cava IVC is then unclamped, allowing normal reperfusive blood flow from the inferior vena cava IVC through the outer tube 12 into the right atrium of the heart HT. The surgeon may then proceed with necessary surgical repair procedures in an essentially bloodless field. The membrane 46 at the trailing end 44 of the inner tube 14 may be penetrated by any relatively large bore needle to allow infusion of fluids as necessary or desirable.

Following the surgical operation, the shunt 10 is withdrawn from the patient by discontinuing the Pringle maneuver, returning the inner tube 14 into its fully inserted position within the outer tube 12 to close all of the openings 34 in the outer tube 12, deflating the balloons of the cuffs 20, 22 and then withdrawing the shunt 10 through the venotomy V, after which the venotomy is closed.

The dimensional considerations in construction of the shunt 10 should be apparent to those persons skilled in the art. The outer diameter of the outer tube 12 must of course be at least slight smaller than the average diameter of the lumen of the patient's inferior vena cava IVC. The overall length of the outer tube 12 must be sufficient to extend from within the right atrium of the heart HT to and outwardly from the suitable venotomy area of the patient's inferior vena cava IVC. Finally, the spacing between the cuffs 20, 22 must be sufficient to be at least slightly greater than the distance between the patient's atrial-caval opening ACO and the juncture of the hepatic veins HV with the inferior vena cava IVC, but less than the distance between the atrial-caval opening ACO and the renal veins RV. On the other hand, it is contemplated that the shunt 10 may be constructed of a significantly greater length and with the cuffs 20, 22 spaced apart by a dimension at least slightly exceeding the distance between the patient's atrial-caval opening ACO and the juncture of the patient's renal veins RV and the inferior vena cava IVC, so that the shunt 10 may be utilized to also isolate the kidneys K and renal veins RV. A shunt of such greater dimensions would also be suitable for surgical operations when the retro-caval injuries are extensive. It is also contemplated that with many patients, the inferior vena cava is of sufficient length between the hepatic veins and the atrial-caval opening into the right atrium of the heart to accommodate the cuff 20 so that a shunt of the type of the present invention may be configured and dimensioned for insertion into the inferior vena cava of the patient with the cuff 20 disposed within the lumen of the cava upstream of the hepatic veins HV but without the necessity of advancing the cuff 20 into the right atrium of the heart HT. Ideally, the shunt 10 would be produced in differing sizes for use with differing adult, child and infant patients, based upon biostatistical averages.

As will be understood by those persons skilled in the art, the present shunt offers a number of advantages over the prior art devices discussed above. Most importantly, the present shunt is very easy and simple to utilize, especially in that the insertion and operation of the shunt does not require the use of umbilical tapes or other associated devices or surgical techniques which require particular skill and experience, so that substantially any surgeon including surgeons who are not particularly experienced in trauma surgery can readily utilize the shunt. Reperfusion of the kidneys and extremities is easily and optimally accomplished. Moreover, the time required for insertion of the shunt is minimal and greatly reduced in comparison to conventional surgical techniques, so that it is hoped that the shunt would enable further improvements in the rates of mortality experienced in surgery of traumatic abdominal injuries. A shunt of the present construction could also be utilized in various elective surgical procedures involving a need to isolate the liver and hepatic veins and, as necessary, a shunt of specialized dimensions could be fabricated in advance to better facilitate such surgeries. Furthermore, it is contemplated that a modified construction of the present shunt could be utilized in performing liver transplants. For example, the outer tube of the shunt could be made in two end-abutting pieces to be capable of separation from one another. The shunt would be inserted in the recipient patient when his or her liver is removed. When the donor liver is to be placed in the recipient, the two component pieces of the outer tube would be separated so that the vena cava accompanying the donor liver could be inserted over the two components. Other potential uses for the present shunt may also occur to those persons skilled in the art.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A shunt for use in human surgical operations for isolating the liver and its hepatic veins from reperfusion of blood through the inferior vena cava, the shunt comprising:

an outer tube having a leading end for insertion into and advancement through the inferior vena cava from a selected venotomy location downstream of the hepatic veins to a location upstream of the hepatic veins and having a trailing end for disposition outside the inferior vena cava, a first radially outwardly expansible cuff affixed to the outer tube adjacent the leading end thereof for sealing engagement with the inferior vena cava at the upstream location, a second radially outwardly expansible cuff affixed to the outer tube at an intermediate location therealong spaced from the first cuff for sealing engagement with the inferior vena cava at a location downstream of the hepatic veins and upstream of the venotomy location, the outer tube having at least one opening formed therethrough between the second cuff and the trailing end of the outer tube for disposition within the inferior vena cava, an inner tube telescopically movable within the outer tube and having an operating end extending outwardly from the trailing end of the outer tube for actuating movement of the inner tube relative to the outer tube, and at least a pair of annular sealing rings respectively attached exteriorly to the inner tube at a spacing therealong greater than the lengthwise extent of the opening in the outer tube, whereby the cuffs prevent blood reperfusion through the inferior vena cava between the hepatic veins and the heart as well as backflow of blood downstream from the hepatic veins and selective movement of the inner tube with respect to the outer tube opens and closes the opening in the outer tube to selectively control fluid communication between the inferior vena cava and the interior of the outer tube for controlling normal blood reperfusion from the lower extremities.

2. A shunt according to claim 1 and characterized further in that the spacing of the second cuff from the first cuff is selected for disposition of the second cuff downstream of the hepatic veins and upstream of the renal veins from the kidneys when the first cuff is at the upstream location in sealing engagement with the inferior vena cava.

3. A shunt according to claim 2 and characterized further in that the outer tube has a plurality of openings formed therethrough at spacings along the length thereof, at least one of the openings being sufficiently adjacent the second cuff to be upstream of the renal veins for blood reperfusion from the kidneys and their renal veins into the interior of the outer tube when the inner tube is moved to open the one opening in the outer tube.

4. A shunt according to claim 3 and characterized further in that a plurality of the sealing rings are attached at spacings exteriorly to the inner tube in correspondence to the openings in the outer tube.

5. A shunt according to claim 1 and characterized further in that each cuff is inflatable.

6. A shunt according to claim 5 and characterized further by means associated with the outer tube for defining respective passageways communicating with the first and second cuffs for admitting thereinto and exhausting therefrom inflating fluid.

7. A shunt according to claim 1 and characterized further in that the operating end of the inner tube is closed by a penetrable membrane for preventing blood loss through the inner tube while permitting selective fluid injections into the inner tube.

8. A shunt according to claim 1 and characterized further in that the inner and outer tubes are formed of a flexible material.

9. A shunt according to claim 1 and characterized further in that the outer tube has a plurality of openings formed therethrough at spacings along the length thereof.

10. A shunt according to claim 9 and characterized further in that a plurality of the sealing rings are attached at spacings exteriorly to the inner tube in correspondence to the openings in the outer tube.

* * * * *

UNITED STATES PATENT AND TRADEMARK OFFICE
CERTIFICATE OF CORRECTION

PATENT NO. : 4,950,226

DATED : August 21, 1990

INVENTOR(S) : Bruce Barron

It is certified that error appears in the above-identified patent and that said Letters Patent is hereby corrected as shown below:

Column 4, Line 32, reads "opening" but should read -- openings --.

Column 4, Line 54, reads "t" but should read -- to --.

Column 4, Line 58, after "spacings" delete -- u --.

Column 5, Line 15, after "FIG. 2" add -- . --.

Column 5, Line 33, after "heart" add -- . --.

Column 5, Line 48, reads "momentum" but should read -- omentum --.

Signed and Sealed this

Twenty-second Day of September, 1992

Attest:

DOUGLAS B. COMER

Attesting Officer

Acting Commissioner of Patents and Trademarks